United States Patent [19]

Spanko

[11] Patent Number: 4,576,576
[45] Date of Patent: Mar. 18, 1986

[54] MEASUREMENT TEMPLATES FOR A DENTAL RESTORATION

[76] Inventor: Jacob E. Spanko, The Bigelow, 622, Pittsburgh, Pa. 15219

[21] Appl. No.: 703,757
[22] Filed: Feb. 21, 1985
[51] Int. Cl.$^4$ ............................................. A61C 19/04
[52] U.S. Cl. ........................................ 433/72; 433/56
[58] Field of Search .................................. 433/72, 56

[56] References Cited

U.S. PATENT DOCUMENTS 2,016,103  10/1935  Chott ................................... 433/56

FOREIGN PATENT DOCUMENTS 2909719  9/1980  Fed. Rep. of Germany ........ 433/56

Primary Examiner—Robert Peshock
Attorney, Agent, or Firm—Reed, Smith, Shaw & McClay

[57] ABSTRACT

An article of manufacture for planning the restoration of an irregular dentition and being adapted for bilateral use comprising a rigid, formed template presenting an upper concave surface to the viewer while it is positioned above the model of the lower dentition of a patient; the mesial edge of the template is substantially linear and spaced apart from the lingual aspect of the anterior teeth. The proximal edge of the template is spaced apart from the mesial edge sufficiently to extend beyond the third molars. The opposing lateral edges of the template are flanged outwardly from the mesial edge to the distal edge to parallel the diverging dentition and both joining the distal edge; and the concave/convex of the template are of a preset substantially uniform curvature with the radius of the upper surface chosen to correspond to one of the variable radius, curves of Spee and Wilson normally occurring in an existing dentition under analysis.

8 Claims, 8 Drawing Figures

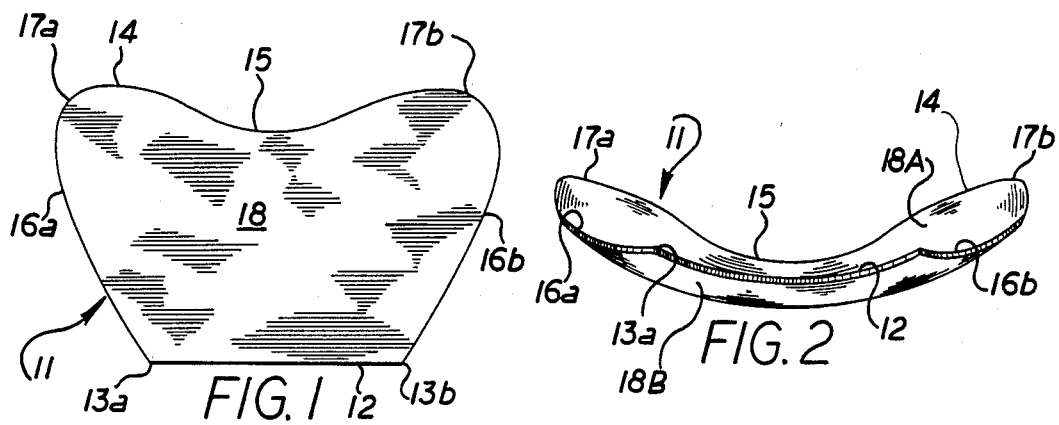
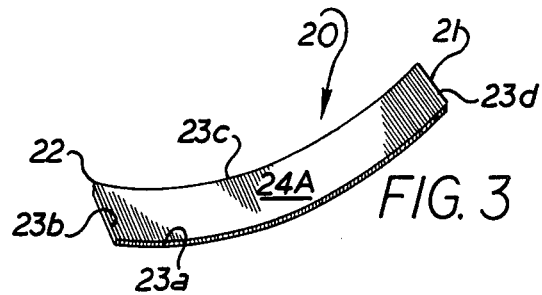
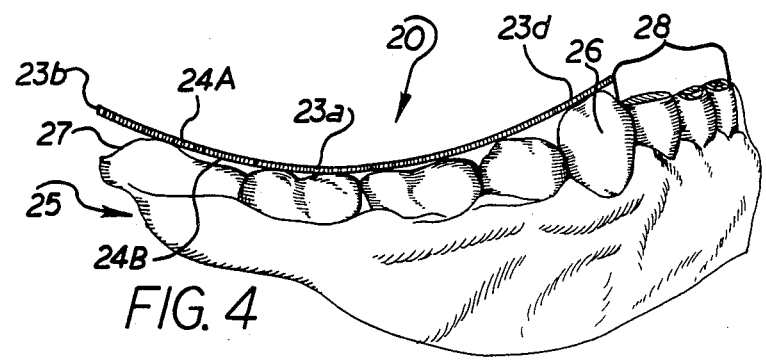
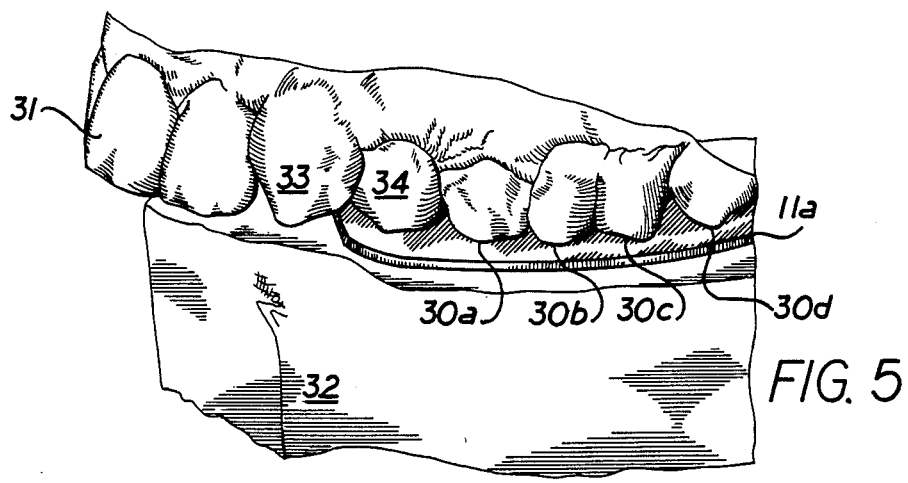

MEASUREMENT TEMPLATES FOR A DENTAL RESTORATION

FIELD OF THE INVENTION

This invention relates to the important measurement of variations found in the planes of occlusion of a human dentition. In another aspect, it relates to a set of various configuration templates designed for determining the existing curves formed by the cusps of the teeth, preparatory to their restorative dentistry for improved biting efficiency.

BACKGROUND OF THE INVENTION

The tips of the cusps of the teeth form a curve from the front to the back of the mouth. This anterior-posterior curve is called the curve of Spee. The same cusps form a curve from the right to the left, or across the mouth, called the curve of Wilson. By convention, these curves do not include the six (6) anterior teeth (which normally overlap upon occlusion). So, these curves are defined as beginning at the distal aspect of the cuspid or canine tooth.

In planning the reconstruction of a dentition, with either crowns, or fixed or removable partial dentures, or complete dentures, these curves must be analyzed and modified to eliminate any trauma to a tooth, or group of teeth, both in vertical position and lateral movements.

If a line is drawn across the cusp tips of the posterior or back teeth, it forms an arc or a portion of a circle that can be measured as the radius of that circle, this radius normally may vary from a three inch radius to an essentially flat surface. It is historically evaluated, by trial and error archial analysis with calipers or exotic, expensive analysis equipment.

In restorative dentistry, elongating, shortening or extracting a tooth, or teeth, may be necessary to prevent the opposing tooth or teeth from locking, tripping, or causing trauma to the teeth, supporting structures and joint.

The use of templates is a quick, simple, economical system of diagnosing curves, and establishing cusp height in the course of fabricating crowns, inlays, bridges, partials and full dentures.

OBJECTS OF THE INVENTION

It is an object of the invention to provide an alternative and novel economical device for measuring and planning the restoration of an irregular dentition. It is another object to provide simply employed devices to quickly determine the curves of Spee and Wilson for planning the corrective restoration. It is still another object to provide means for establishing cusp height in the fabrication of crowns, inlays, bridges and dentures.

It is a yet further object to provide a set of curved measurement articles which are capable of multiple applications in dental model analyses for restorative dental work. A still further object is a treatment plan for corrections of malocclusions that is permanently recorded in the patient's dental history and is easily communicated to a dental laboratory technician.

The dentist selects the radius of template as predetermined by cusp analysis. He communicates this radius by prescription to the dental laboratory technician, for precise cusp placement on the fabricated dental restorations. The dentist can evaluate the completed restorations as returned from the laboratory by use of the preselected radius template.

SUMMARY OF THE INVENTION

The invention comprises two sets of templates, one is for a complete arch and suited for bilateral use; that is, when the left and right sides of the dentition are substantially symmetrical. The other set is for use in unilateral curve determination, when the patient's dentition is not symmetrical as to the opposite side. Each set of templates has several essentially matching peripheral configurations. Each member of the set has a preset varied degree of curvature (concavity) such that one of the templates is essentially planar and the balance extending from radii of ten down to three inches. One template of each set will aproximately correspond to the curves of Spee (or Wilson) of a patient's dentition. These templates are tried and positioned in order on a dental model to quickly evaluate the radius of the cusp curves as presented by the patient, and thus permit a facile diagnosis of what changes are necessary to achieve, by restorative work on the dentition, the cusp curves which are physiologically acceptable and most efficient for the patient.

One embodiment of the template is intended for full mouth determination. It comprises a rigid preformed template presenting a uniformly concave surface to the viewer while it is positioned above the model made from the lower dentition of a patient; the mesial (forward) edge of the template being substantially linear and spaced apart in use from the lingual (tongue-side) aspect of the anterior teeth, and spaced apart from the mesial edge to extend distally beyond the position of the cusp of the third molar and optionally the distal (rearward) edge of the template being inwardly sloped to define an essentially symmetrical recess.; the opposing lateral edges of the template are flanged outwardly from the mesial edge to the distal edge so as to parallel the diverging dentition and are joined at the distal edge in a conveniently rounded corner. The convex lower surface of the template is of a preset substantially uniform curvature with the radius of said surface being chosen to correspond to one of the variable curves of Spee and Wilson. These curves, normally occurring in an existing dentition under analysis, serve as to measure variations from an ideal occlusion of the teeth when there is contact of the upper and lower arches of the dentition.

In the other template embodiment, which is intended for a single arch determination (either upper or lower quadrant), the template comprises a rigid preformed template presenting a uniformly concave, upwardly facing surface to the viewer when it is aligned between the opposing lower and upper quadrants of the unilateral dentition and a convex surface on the lower teeth. The template is provided with a substantially rectangular broader face adapted to abut the posterior teeth but is of a length chosen so as not to overlap the six (6) normal anterior teeth nor to extend distally beyond the position of the cusp of the third molar; the vertical edges of the template are of a markedly smaller dimension than the horizontal faces; and the concave upper surface and its complementary convex lower surface of said template are of a preset substantially uniform curvature with the radius of that inside surface being chosen to correspond to one of the variable curves of Spee and Wilson normally occurring in any given existing dentition under analysis.

In a preferred embodiment, each template, as sold for professional use, includes a pre-imprinted number identifying the radius of its uniform curvature.

These and other objects and advantages are accomplished by studying the following detailed description, set forth in conjunction with the accompanying drawing of several figures, in which like parts are identified by like reference numerals and further in which:

FIG. 1 is a top plan view of one embodiment of a full mouth dentition measuring template of the present invention;

FIG. 2 is a front elevation view of the template of FIG. 1, depicting its predetermined concave upper surface and convex lower surface;

FIG. 3 is perspective view of one embodiment of the single arch (partial) mouth template of the present invention;

FIG. 4 is perspective view of the single arch template of FIG. 3 positioned over the right side of the lower human teeth model and defining the patient's particular curve of Spee;

FIG. 5 is a perspective view of a full-mouth template partly seen contacting the cusps of the upper left side of the human teeth model and indicating the restorative denistry to be afforded the patient;

DETAILED DESCRIPTION OF THE INVENTION

Figure 6:
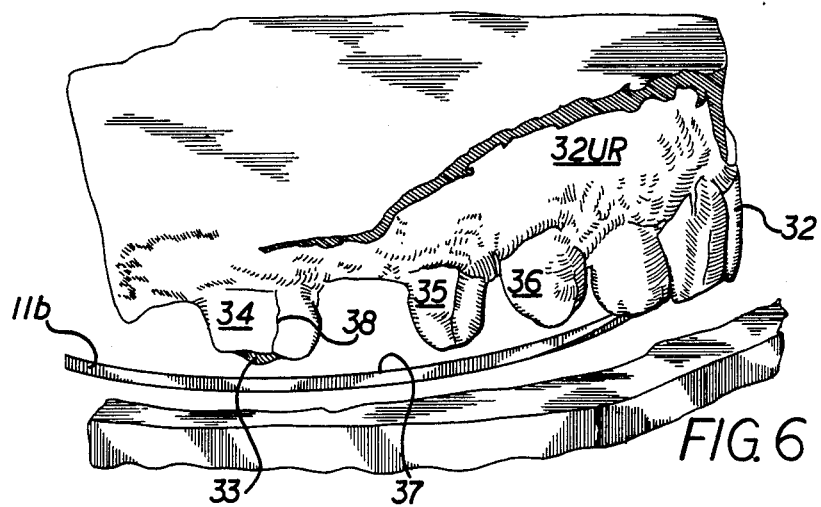
FIG. 6 is a perspective view of the same full-mouth template partly seen contacting the cusps of the upper right side of the human teeth model and indicating the restorative dentistry on that portion of the natural dentition.

Referring now to the drawing, and to FIG. 1 in particular, a top plan view of the complete template 11 is seen with its mesial edge 12 downward. This edge would be placed forwardly in the mouth model (not shown) with its mesial corners, 13a and 13b, resting directly behind the anterior teeth, specifically behind the distal aspect of each cuspid tooth. The opposing (or distal) edge 14 of template 11 is provided with an inwardly sloped recess 15, essentially symmetrical.

The opposing lateral edges, 16a and 16b, of the template are flanged outwardly from the mesial to the distal edges so as to parallel the diverging dentition and to provide overlap thereof. These lateral edges and distal edge join in optionally rounded corners, 17a and 17b.

In FIG. 2, the concave upper surface 18A and convex lower surface 18B of the full-arch template 11 becomes most apparent. The preset uniform curvatures of surfaces 18 define for this specific embodiment, a radius of about three inches, the calculation and importance of which measurement is to be explained. The anterior to posterior curve (of Spee) corresponds to the concave curvature of the lateral edges 16a and 16b while the cross-arch curve (from left to right) of Wilson corresponds to the curvature of the mesial and distal edges, 12 and 14, respectively.

When a template is placed on a plaster cast model of a patient's existing dentition, the irregularities of that dentition from the ideal curve of the cusps become evident to the dentist in his analysis of the dentition for potential restoration work.

In FIG. 3 is seen a perspective view of the other major embodiment of this invention, termed a single-arch template, used for each side of the dentition individually, when the case does not present symmetrical curves from one side to the other. Template 20 is of a substantially rectangular configuration as to its broader face, with a length dimension thereof exceeding the width dimension by a factor of 5 to 7, and preferably being about 6. The overall length is chosen for one narrow end 21 to abut the distal aspect of the cuspid tooth and the other narrow end 22 should extend to a position of overlap of the cusps of the third molar (each not shown).

The vertical edges, 23a through 23d, of template 20 are of a markedly smaller dimension than the essentially horizontally disposed faces, with the width dimension exceeding the depth dimension by a factor of 14:1 to 3:1 and preferably about 7:1.

The uniform concavity of the upper surface 24A, and convexity of lower 24B, is more apparent in FIG. 4, wherein it is positioned in contact with the lower right-side segment of a partial dentition model, generally 25. Note that the template 20 extends from over the first bicuspid 26 backward to overlap the third molar 27, with the anterior three teeth 28 (the incisors and cuspid) being out of contact with the template when occlusion of the model in conventional articulator is effected (not shown).

FIGS. 5-8 are described in relation to several case studies on how to professionally use the novel single-arch and full-mouth templates in planning restorative dentistry.

EXAMPLE 1

There is shown in FIG. 5, a perspective view of a full-mouth template 11a contacting the cusps 30a to 30d of the upper left quadrant of a teeth model 31, thus presenting a (mal) occlusion for analysis. Block 32 supports the template 11a, simulating the omitted lower dentition normally abutting the upper quadrant. The presentation of the right hand side of the same arch and template is not seen since the analysis indicated that no restorative work on the cusps was called for. However, the depicted case shows that the first bicuspid, 34, is too short and crooked to make the cusps symmetrical and functional. The indicated restoration work is to lengthen it with a restoration inlay work so that it contacts the template. This will result in a proper occlusion and contact for the opposing cusps.

EXAMPLE 2

There is shown in FIG. 6 a perspective view of another employment of a full template 11b with a different unilateral dentition 32, with an irregularity being determined for the upper right side quadrant 32UR. This case shows that if the lingual cusp 33 on first molar 34 is shortened, then the cusps of the first bicuspid 35 and the cuspid 36 will come into the curve 37 (plane) of occlusion defined by template 11b. Therefore, molar 34 will not continue to be traumatized during biting, and should avoid a repetition of the existing vertical fracture 38, which will also need to be repaired (if restoration is to be carried out).

EXAMPLE 3

Figure 7:
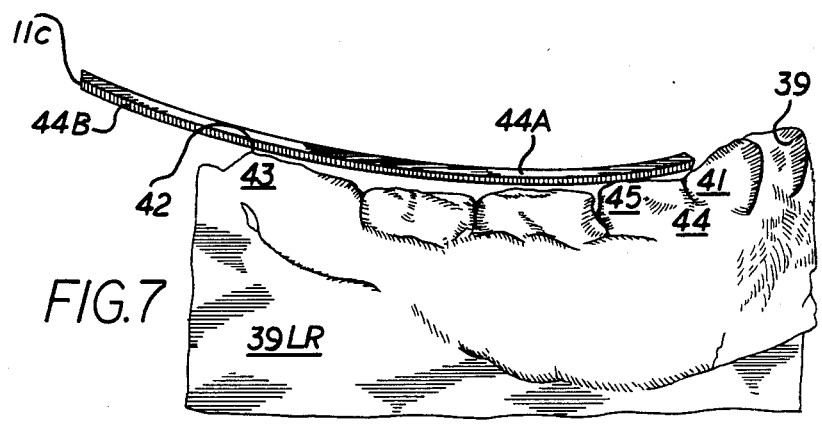
FIG. 7 is a perspective view of the novel template of single arch, four inch radius, disposed on the lower right side of a dentition model, and defining the optimum curve of Spee to be gained by restorative denistry.

There is next shown in FIG. 7 a perspective view of the novel single arch (unilateral use) template 11c aligned on the lower right quadrant of a denture model 39LR of a different case (unsymmetrical curves) employing a four inch radius template bar. This radius defines the optimum curve for restoration here, since the two inch radius curve did not touch the distal aspect of the cuspid 41, and the three inch curve would be acceptable only if the cusp 42 of third molar 43 were shortened. Diagnosis determined that the four inch curve template 11c should start at the distal aspect 44 of cuspid 41, and that the opposing upper bicuspid (not shown) needs to be crowned so as to lengthen it and to occlude properly with the lower bicuspid 45.

EXAMPLE 4

Figure 8:
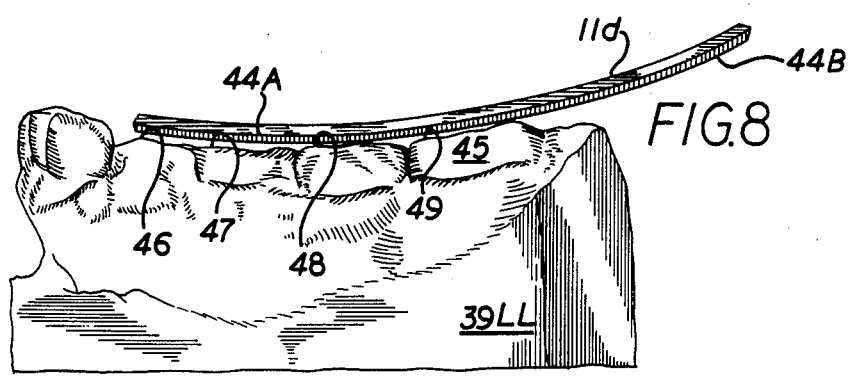
FIG. 8 is a perspective view of the same single arch template disposed over the lower left side denture model revealing the appropriate restorative denistry performable thereon.

There is shown in FIG. 8 a perspective view of the single arch template 11d, now aligned on the lower left quadrant of the same dentition model 39LL which is the complement of FIG. 7 (Example 3). The four inch template 11d defines the optimum curve of Spee 44a on this quadrant. The diagnosis here ascertained that only lower second molar 45 and the molar above it (not seen) require restoration. This was done by lowering the four inch curvature defined by teeth cusps 46, 47, 48, and 49, until all cusp tips come into contact of a common plane 44a for this preferred radius.

While the present invention discloses two forms of templates in which the preferred embodiments depicted in the drawings have the upper and lower surfaces (18A and 18B in FIG. 2, and 44A and 44B in FIG. 7), which while being spaced apart do essentially conform in surface curvature to one another, this is not necessary for the practice of this invention in all types of measurements. It is feasible to have the upper surface 18A in FIG. 2, and the upper surface 44A in FIG. 7 fabricated so as to be substantially planar (flat) in configuration, when the restorations work focuses on only the lower complete arch. Of course, if the upper arch is the focus of the determination of the variations of the curves of the cusp tips, then the upper surface of the templates also need to be configured to preset uniform curvatures correlating with the discussed curves of Spee and Wilson. Such a modification is within the teaching and scope of this invention but provides templates which are useful only in lower dentition analysis.

While in the foregoing, preferred embodiment of the invention has been described, it should be understood to one skilled in the art that various modifications and changes can be made without departing from the true spirit and scope of the invention as recited in the appended claims.

I claim:

1. An article of manufacture for planning the restoration of an irregular dentition involving determination of the actual curves defined by the cusps of the teeth of the natural dentition and being adapted for bilateral use on a dentition model comprising:
   a. an essentially rigid, preformed template presenting a first and second surface with said first and lower surface being convex in relation to said second surface and being spaced apart therefrom but substantially conforming to the curvature of said second surface;
   b. the mesial edge of the template being substantially linear and spaced apart in use from the lingual face of the anterior teeth;
   c. the distal edge of the template being spaced apart from the mesial edge sufficiently to extend distally beyond the third molar;
   d. the opposing lateral edges of the template being flanged outwardly from the mesial edge to the distal edge to parallel the diverging quadrants of the dentition model with both joining the distal edge in non-pointed corners; and
   e. in which at least said first surface presents a preset substantially uniform curvature with the radius of said convex surface chosen to correspond to one of the variable radius curves limited by and to be established for the existing dentition under analysis, and further wherein the anterior to posterior curvature thereof corresponds to an ideal curve of Spee of a defined radius, and wherein the cross-denture arch curvature thereof corresponds to an ideal curve of Wilson of a defined radius.

2. The article of claim 1 wherein said distal edge is sloped inwardly along its length to define a substantially symmetrical recess.

3. A plurality of the article of claim 1 with each member thereof having a preset degree of curvature ranging from essentially flat to radii of curvature ranging between ten and three inches.

4. The article of claim 1 wherein the horizontal width dimension exceeds the depth dimension by a factor ranging from 14:1 down to 3:1.

5. An article of manufacture for planning the restoration of an irregular dentition involving determination of the actual curves defined by the cusps of the teeth in a model of the existing dentition and being adapted for unilateral measurement on a dentition model comprising:
   a. an essentially rigid preformed template presenting a first and second surface with said first and lower surface being convex in relation to and said second surface and being spaced apart therefrom but substantially conforming to the curvature of said first surface when positioned on one quadrant of a dentition model;
   b. the template having a substantially rectangular broader face adapted to abut the posterior teeth but of a length chosen not to overlap the normal anterior teeth or to extend distally to a position much beyond the cusp of the third molar;
   c. the vertical edges of the template are of a markedly smaller dimension than the horizontal faces; and
   d. in which at least said first surface of the template presents a preset substantially uniform curvature with the radius of said convex surface chosen to correspond to one of the variable radius curves limited by and to be established for the existing dentition under analysis, and further wherein the anterior to posterior curvature thereof corresponds to an ideal curve of Spee of a defined radius.

6. The article of claim 5 wherein the length dimension exceeds the width dimension by a factor ranging from five to seven.

7. A plurality of the article of claim 6 with each member thereof having a preset degree of curvature ranging from essentially flat to radii of curvature ranging between ten and three inches.

8. The article of claim 5 wherein the horizontal width dimension exceeds the depth dimension by a factor ranging from 14:1 down to 3:1.

* * * * *